(12) United States Patent
Wilson et al.

(10) Patent No.: US 6,993,144 B1
(45) Date of Patent: Jan. 31, 2006

(54) INSERT EARPHONE ASSEMBLY FOR AUDIOMETRIC TESTING AND METHOD FOR MAKING SAME

(75) Inventors: Donald L. Wilson, Barrington, IL (US); Steven J. Iseberg, Palatine, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 704 days.

(21) Appl. No.: 09/676,722

(22) Filed: Sep. 28, 2000

Related U.S. Application Data

(60) Provisional application No. 60/156,777, filed on Sep. 30, 1999.

(51) Int. Cl.
*H04R 25/00* (2006.01)

(52) U.S. Cl. ..................... 381/380; 381/328

(58) Field of Classification Search .............. 381/60, 381/328, 380, 325, 374, 381, 382, 330, 309, 381/370, 338; 600/559; 73/585; 181/130, 181/129, 128, 135; 379/430
See application file for complete search history.

(56) References Cited

U.S. PATENT DOCUMENTS

| | | | |
|---|---|---|---|
| 2,430,229 A | 11/1947 | Kelsey |
| 2,971,065 A | 2/1961 | Busse |
| 3,408,461 A | 10/1968 | Langford |
| 3,529,102 A | 9/1970 | Rosenstand |
| 3,671,685 A | 6/1972 | McCabe |
| 3,789,164 A | 1/1974 | Ryder |
| 3,819,860 A | 6/1974 | Miller |
| 4,170,720 A | 10/1979 | Killion |
| 4,447,677 A | 5/1984 | Miyahra et al. |
| 4,520,236 A | 5/1985 | Gauthier |
| 4,592,087 A | 5/1986 | Killion |
| 4,646,872 A | 3/1987 | Kamon et al. |
| 4,677,675 A | 6/1987 | Killion et al. |
| 4,677,679 A | 6/1987 | Killion |
| 4,689,819 A | 8/1987 | Killion |
| 4,739,512 A | 4/1988 | Hartl et al. |

(Continued)

FOREIGN PATENT DOCUMENTS

CH 648 172 A5 2/1985

(Continued)

OTHER PUBLICATIONS

E-A-R, Instructions for the use of E-A-RTONE 3A Insert Earphones, 1995, 1990, Aearo Company Auditory Systems, p. 1-8.*

(Continued)

*Primary Examiner*—Laura A. Grier
(74) *Attorney, Agent, or Firm*—McAndrews, Held & Malloy, Ltd.

(57) ABSTRACT

An improved insert earphone for audiometric testing is provided, having a housing, a receiver located within the housing, a flexible eartip located externally to the housing, and a tube nipple acoustically coupled between the receiver and the flexible eartip. The flexible eartip has a flexible tube portion that is coupled to an output end of the tube nipple, which may be rigid. The housing and tube nipple are configured and arranged such that the angle between a longitudinal axis of the tube nipple and the vertical axis is obtuse, minimizing the stress on the ear canal when the flexible eartip is inserted therein. An acoustic damper may be located at or near the input end of the tube nipple to prevent ear wax from clogging the damper and minimize the need for damper replacement.

31 Claims, 11 Drawing Sheets

U.S. PATENT DOCUMENTS

| | | | |
|---|---|---|---|
| 4,763,753 A | | 8/1988 | Killion |
| 4,781,196 A | | 11/1988 | Killion |
| 4,852,177 A | | 7/1989 | Ambrose |
| 4,852,683 A | | 8/1989 | Killion |
| 4,870,688 A | | 9/1989 | Voroba et al. |
| 4,880,076 A | | 11/1989 | Ahlberg et al. ............. 181/130 |
| 5,099,856 A | | 3/1992 | Killion et al. |
| 5,113,967 A | | 5/1992 | Killion et al. |
| 5,128,566 A | | 7/1992 | Killion et al. |
| 5,131,046 A | | 7/1992 | Killion et al. |
| 5,144,675 A | | 9/1992 | Killion et al. |
| 5,265,168 A | * | 11/1993 | Schiess et al. ................ 381/69 |
| 5,395,168 A | * | 3/1995 | Leenen ...................... 381/68.6 |
| 5,781,638 A | * | 7/1998 | Hosaka et al. .............. 381/322 |
| 5,790,672 A | * | 8/1998 | Klostermeier ................ 381/69 |
| 5,887,070 A | * | 3/1999 | Iseberg et al. .............. 381/380 |
| 5,917,918 A | * | 6/1999 | Callahan ..................... 381/67 |
| 5,982,908 A | * | 11/1999 | Bauman ..................... 381/325 |
| 6,009,183 A | * | 12/1999 | Taenzer et al. ............. 381/330 |
| 6,473,512 B1 | * | 10/2002 | Juneau et al. ............... 381/328 |
| 6,671,381 B1 | * | 12/2003 | Lux-Wellenhof ........... 381/325 |

FOREIGN PATENT DOCUMENTS

| | | | |
|---|---|---|---|
| CH | 648172 | * | 2/1985 |
| GB | 2155276 | | 9/1985 |
| JP | 0043700 | | 3/1983 |
| JP | 0238196 | | 10/1986 |
| JP | 0290295 | | 12/1987 |

OTHER PUBLICATIONS

Knopf Im Ohr, pp. 34, 354 Audio Jul., 1993.
Little Feat, p. 36, Audio Jul., 1993.
Pp. 135, 136, Audio Jul., 1993.
M.C. Killion: "An 'Acoustically Invisible' Hearing Aid", Hearing Instruments, vol. 39, No. 10, 1988.
M.C. Killion, T.W. Tillman, "Evaluation of High-Fidelity Hearing Aids", Journal of Speech and Hearing Research, vol. 25, 15-25, Mar., 1982.
M.C. Killion and W.J. Murphy; "Smoothing the ITE Response: The BF-1743 Damped Coupling Assembly" Apr., 1981.

* cited by examiner

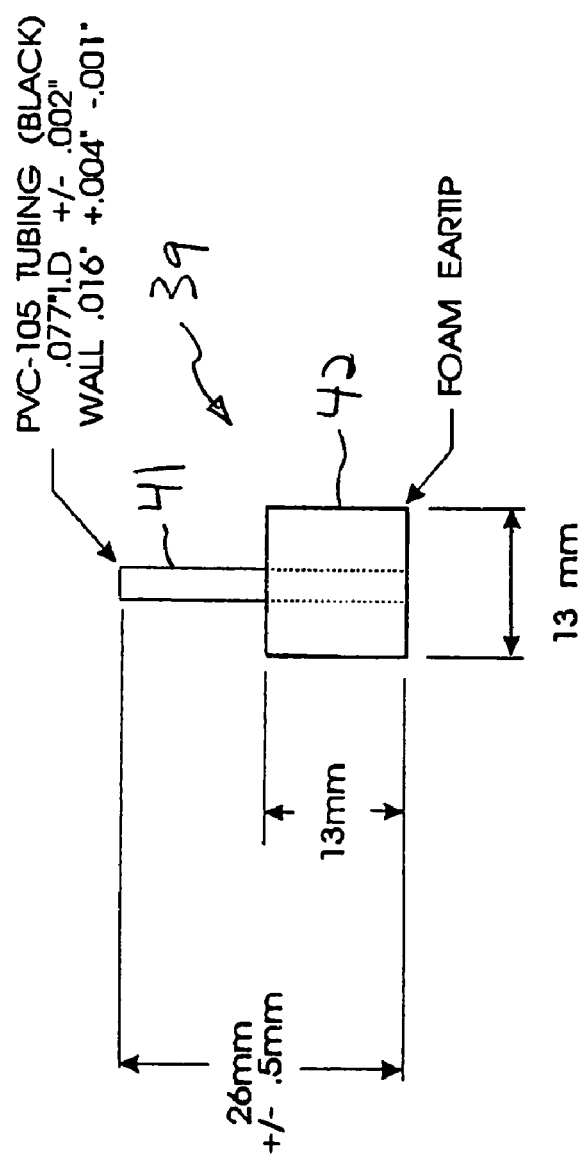
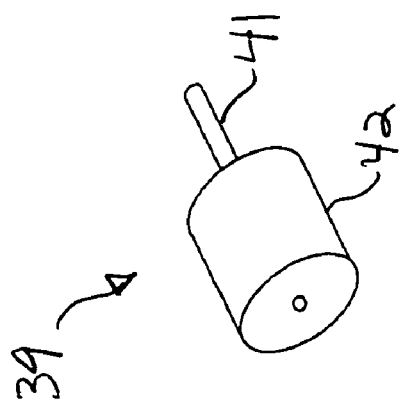
FIG. 3

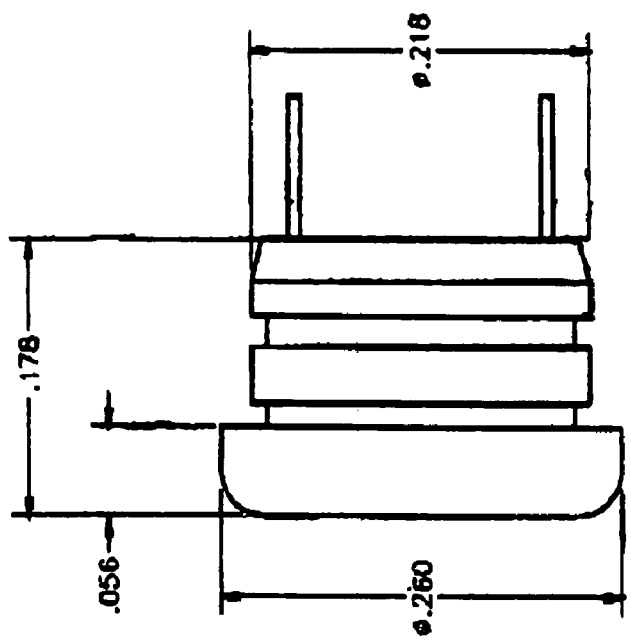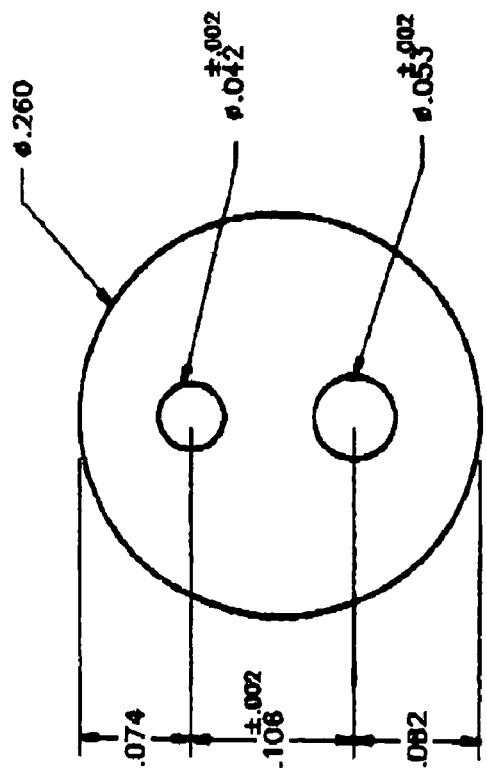
FIG. 4

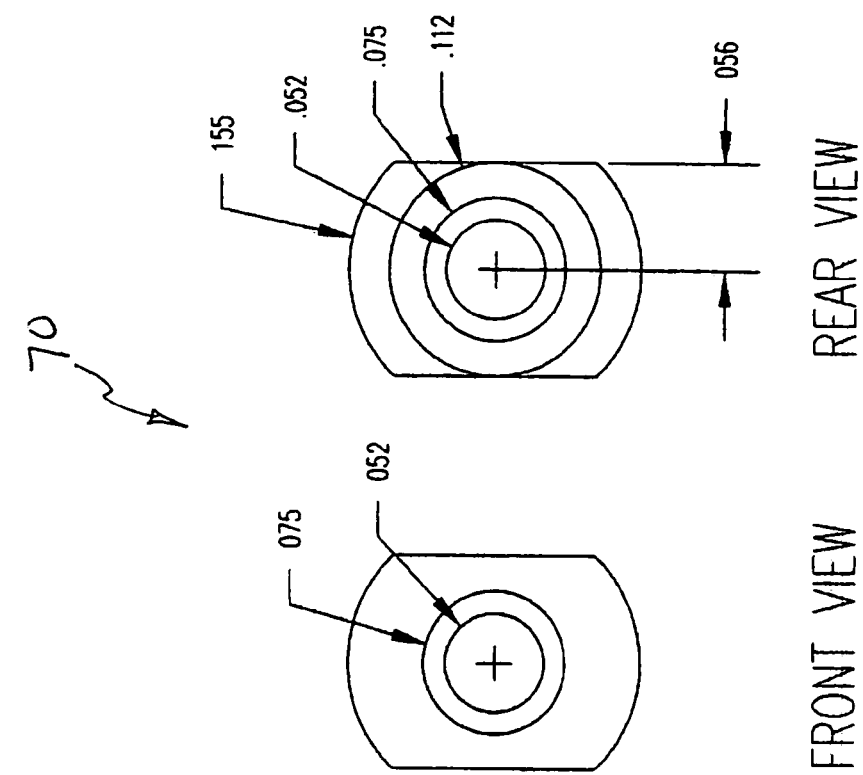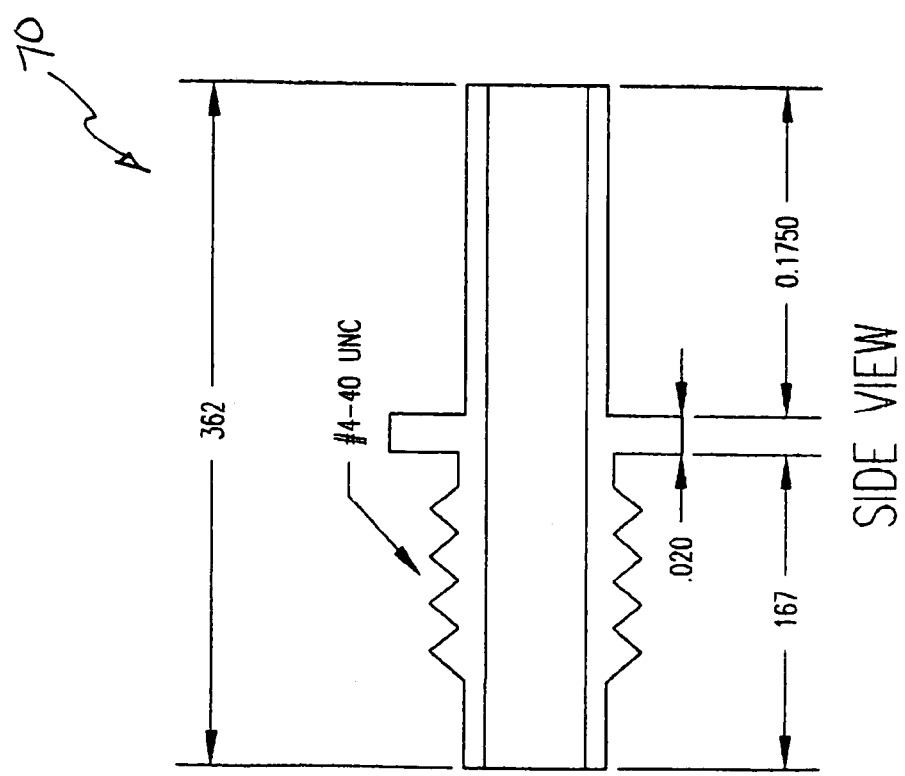
FIG. 7

INSERT EARPHONE ASSEMBLY FOR AUDIOMETRIC TESTING AND METHOD FOR MAKING SAME

CROSS-REFERENCE TO RELATED APPLICATIONS

This application makes reference to, and claims priority to, U.S. provisional application Ser. No. 60/156,777 filed Sep. 30, 1999.

INCORPORATION BY REFERENCE

The above-referenced U.S. provisional application Ser. No. 60/156,777 is hereby incorporated by reference herein in its entirety.

STATEMENT REGARDING FEDERALLY SPONSORED RESEARCH OR DEVELOPMENT

N/A

BACKGROUND OF THE INVENTION

Headphone or earphone devices have been used in audiometry applications for some time. One example of such a device that has been used for many years is the TDH-39 headphone of Telephonics. The TDH-39 headphone basically comprises a metal casing that is worn on the head of a user. The casing is fitted with ear cushions that support the headphone against the outer ear in an attempt to attenuate ambient noise levels during audiometric testing. While the TDH-39 headphone has been widely used and accepted in the audiometry industry, it is quite cumbersome and uncomfortable to wear for extended periods of time and the typical leak around the cushions prevents adequate attentuation of ambient noise. In addition, because the TDH-39 has ear cushions that cover the ear canal, the TDH-39 often causes a canal "collapse" problem which may distort a user's hearing and adversely affect audiometric testing results. While superficial changes have been made to the TDH-39 over the years, such as, for example, the change from a metal to a plastic cased version (i.e., the TDH-39P), none of these changes have solved the comfort and canal collapse problems.

Another example of such a device is the ER-3 earphone of Etymotic Research Inc. The ER-3 device is generally the subject of U.S. Pat. No. 4,763,753, and was introduced as an alternative to the TDH-39 for audiometric testing. The ER-3 comprises a pair of base units that each house a transducer and are each connected to an earpiece via a sound tube. The base units are worn around the neck or shoulder area while the earpieces are inserted into the ear canal of a user. The sound tubes are generally long (e.g., 10.95 inches) to enable the positioning of the transducers a sufficient distance from the ear to minimize any interference when the earphones are used, for example, with electrical response audiometry as discussed in U.S. Pat. No. 4,763,753.

While the ER-3 provides sufficient ambient noise attenuation, is more comfortable to wear over extended periods of time, and addresses the collapsed canal problem, it produces a response that is nearly identical to that produced by the THD-39 except at 6 and 8 kHz. In addition, some audiologists have claimed to have difficulty calibrating the ER-3 at 6 kHz. At 8 kHz, the response of the ER-3 is attenuated to 6 the point that it is out of the calibration range of standard audiometers. As can be seen from the frequency response curves set forth in FIG. 1A, the ER-3 response also becomes somewhat distorted at higher frequencies (e.g., at greater than approximately 6–8 kHz).

A further example of a prior art device is the ER-4 earphone of Etymotic Research Inc. The ER-4 is generally the subject of U.S. Pat. No. 5,887,070, and was developed for hi-fidelity music listening applications. Because the ER-4 does not have enough output to meet the specifications of standard audiometers, however, it is generally not suitable for audiometric testing below approximately 2 kHz.

Further disadvantages and limitations of prior art systems with respect to audiometric testing will become apparent to one of skill in the art through comparison of such systems with the present invention as set forth in the remainder of the present application with reference to the drawings.

SUMMARY OF THE INVENTION

An improved insert earphone for audiometric testing is provided. The insert earphone generally includes a housing, a receiver located within the housing, a flexible eartip located externally to the housing, and a tube nipple. One end of the tube nipple is acoustically coupled to an output port of the receiver and the other end of the tube nipple is acoustically coupled to the flexible eartip. In use, a user places the flexible eartip in the user's ear canal such that the housing is located proximate the user's ear. Electrical signals received by the receiver from an external audio signal source are converted by the receiver into sound. The sound is then transmitted into the ear canal of the user via a sealed acoustic path including the tube nipple and the flexible eartip.

In one embodiment, the housing and tube nipple may be configured and arranged such that an angle between a longitudinal axis of the tube nipple and a vertical axis is obtuse, such as 118 degrees, for example. This configuration and arrangement allows the housing to hang proximate to, and comfortably from, the ear while minimizing the stress applied to the ear canal and/or the eartip.

In another embodiment, the flexible eartip may have a flexible tube portion and a foam eartip portion. The tube nipple, which may be rigid, is coupled to the flexible tube portion of flexible eartip. The flexible tube portion is of a minimum length such that a user may grasp the housing and insert the foam eartip portion of the flexible eartip into the user's ear canal.

In a further embodiment, the tube nipple may have an input end that is located within the housing and coupled to the receiver, and an output end located externally to the housing and coupled to the flexible eartip. The insert earphone may also have an acoustic damper located within the tube nipple at or near the input end of the tube nipple. Such a location of the damper away from the output end of the tube nipple effectively prevents the damper from being clogged with earwax, minimizing the need for damper replacement. Instead, the flexible eartip may be decoupled from the output end of the tube nipple and replaced with a new flexible eartip.

Other aspects, advantages and novel features of the present invention will become apparent from the following detailed description of the invention when considered in conjunction with the accompanying drawings.

BRIEF DESCRIPTION OF THE DRAWINGS

FIG. 3 illustrates detail of one embodiment of the flexible eartip of FIG. 1.

FIG. 4 illustrates detail of one embodiment of the socket of FIG. 1.

FIG. 7 illustrates an alternative embodiment of the tube nipple of FIG. 1.

DETAILED DESCRIPTION OF THE INVENTION

Figure 1A:
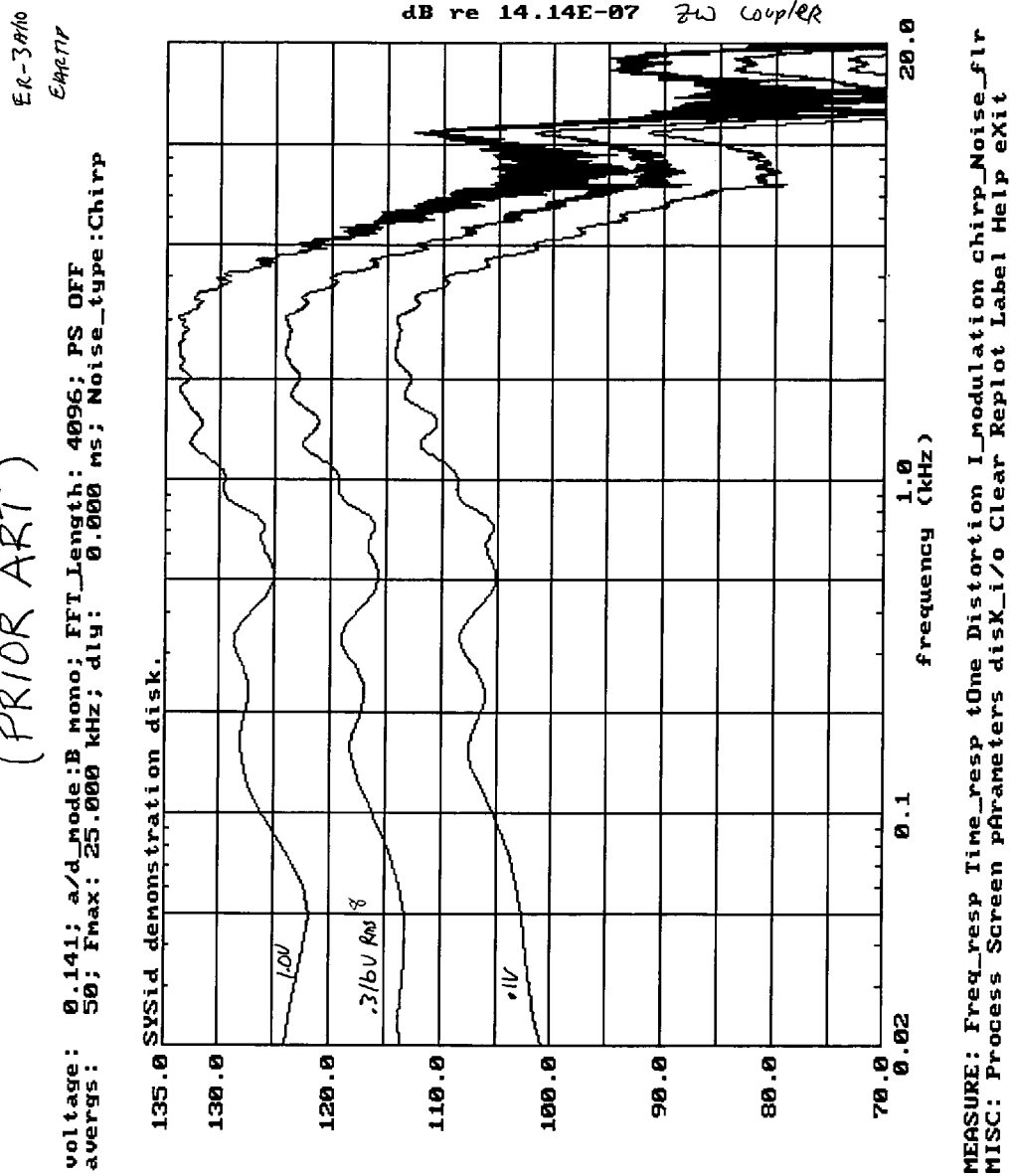
FIG. 1A illustrates frequency response curves of a prior art earphone device.
Figure 1B:
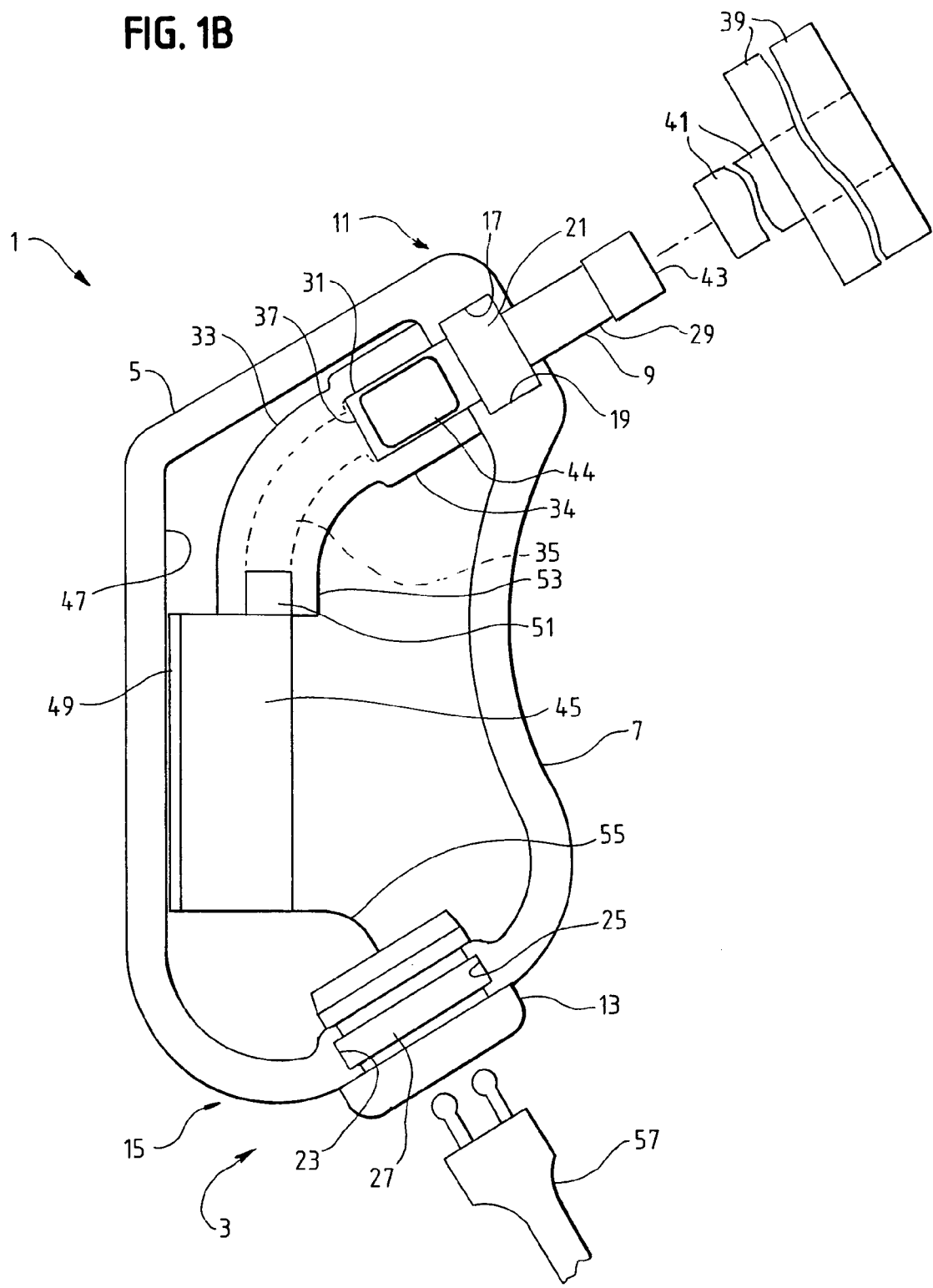
FIG. 1B illustrates an embodiment of an insert earphone assembly built in accordance with the present invention.

FIG. 1B illustrates an embodiment of an insert earphone assembly 1 built in accordance with the present invention. The insert earphone 1 has a unitary housing 3. The unitary housing 3 is formed of two housing components 5 and 7 that snap fit against a rigid tube nipple 9 at a top end 11 of the unitary housing 3 and against a socket 13 at a bottom end 15 of the unitary housing 3. Alternatively, the housing components 5 and 7 may be assembled using screws.

More specifically, housing components 5 and 7 have grooves 17 and 19, respectively, located at the top end 11 of the unitary housing 3 that, upon assembly of the unitary housing 3, engage a flange portion 21 of tube nipple 9. Similarly, housing components 5 and 7 have grooves 23 and 25, respectively, located at the bottom end 15 of the unitary housing 3 that, upon assembly of the unitary housing 3, engage a flange portion 27 of the socket 13. Such a snap fit configuration provides for ease of assembly and disassembly of the unitary housing 3. Tube nipple 9 may be, for example, an ER 3-04 nipple, and socket 13 may be, for example, an MS868 socket, available from Etymotic Research Inc. Tube nipple 9 may also be an integral part of the unitary housing 3. In other words, the tube nipple 9 may be formed as part of the unitary housing 3.

Tube nipple 9 has an outer portion 29 that is located on the outside of unitary housing 3 and an inner portion 31 that is located within the unitary housing 3. Inner portion 31 of tube nipple 9 mates with a flexible tubing 33 located within the unitary housing 3. More particularly, the inner portion 31 of tube nipple 9 is inserted into an output end 34 of a channel in flexible tubing 33. The flexible tubing 33 provides an acoustic seal for an input end 37 of the tube nipple 9.

The outer portion 29 of tube nipple 9 likewise mates with a flexible eartip 39. More particularly, the outer portion 29 of tube nipple 9 is inserted into a tube portion 41 of flexible eartip 39. Tube portion 41 forms an acoustic seal between an output end 43 of tube nipple 9 and the ear canal of a user. Flexible eartip 39 may be, for example, an ER-14 eartip available from Etymotic Research Inc. Other types of eartips may also be used, such as, for example, that shown in our U.S. Pat. No. 5,887,070.

An acoustic damper 44 is preferably located in inner portion 31 of tube nipple 9, near input end 37 of tube nipple 9. It is desirable to locate the acoustic damper 44 as such, i.e., far enough away from the output end 43 of tube nipple 9, so that it does not become clogged from, for example, ear wax. This wax free and simple construction enables the flexible eartip 39 to be replaced after use, and eliminates the need for a separate damper replacement kit such as that sold with prior art devices.

Acoustic damper 44 serves to cancel a resonance at lower frequencies. The remaining horn/resonance effect (e.g., between 3 and 5 KHz) is used to help equalization. Acoustic damper 44 may be, for example, 680 Ω.

A receiver 45 is mounted within unitary housing 3. For example, receiver 45 is mounted on an inner surface 47 of housing portion 5. A shock absorbing material 49 is placed between the surface 47 and the receiver 45 to dampen any vibrations that may be transmitted by the unitary housing 3. The receiver 45 and shock absorbing material 49 may be mounted using glue or other adhesive type material.

Receiver 45 has an output port 51 that mates with the flexible tubing 33. More specifically, output port 51 is inserted into an input end 53 of channel 35 in flexible tubing 33. Flexible tubing 33 provides an acoustic seal for the output port 51 of receiver 45.

Receiver 45 is electrically coupled to an audio signal source such as, for example, an audiometer, via wire 55, socket 13 and cable 57. Cable 57, may be, for example, an ER5-10 cable available from Etymotic Research Inc.

During operation of the earphone assembly, electrical signals representative of sound energy are received from an audio signal source (not shown) and transmitted via cable 57, socket 13 and wire 55 to receiver 45. Receiver 45 transduces the electrical signals received into sound energy and transmits the sound energy through output port 51. The sound energy is then coupled to the ear canal of a user through channel 35 of flexible tubing 33 and through tube nipple 9. As set forth below, the electrical signals received by the receiver 45 may be equalized signals.

Figure 1C:
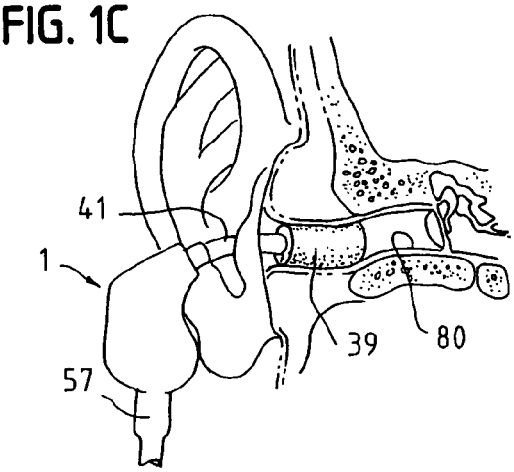
FIG. 1C illustrates full insertion of an embodiment of an insert earphone assembly built in accordance with the present invention.

FIG. 1C illustrates full insertion of an embodiment of an insert earphone assembly built in accordance with the present invention. Referring to FIG. 1C, there is illustrated the insert earphone assembly 1 connected to cable 57 and fully inserted into the ear canal 80 of a user. In accordance with an aspect of the invention, the flexible eartip 39 may be fully inserted into the ear canal 80 and the insert earphone may be supported entirely by the ear canal 80 of the user.

Figure 1D:
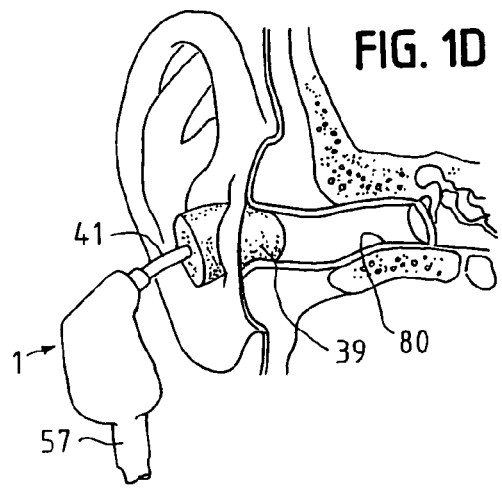
FIG. 1D illustrates shallow insertion of an embodiment of an insert earphone assembly built in accordance with the present invention.

FIG. 1D illustrates shallow insertion of an embodiment of an insert earphone assembly built in accordance with the present invention. Referring to FIG. 1D, there is illustrated the insert earphone assembly 1 connected to cable 57 and partially inserted into the ear canal 80 of a user. In accordance with an aspect of the invention, for shallow insertion of the earphone 1, the flexible eartip 39 may be partially inserted into the ear canal 80. The insert earphone 1, however, may still be supported entirely by the ear canal 80 of the user.

Figure 2:
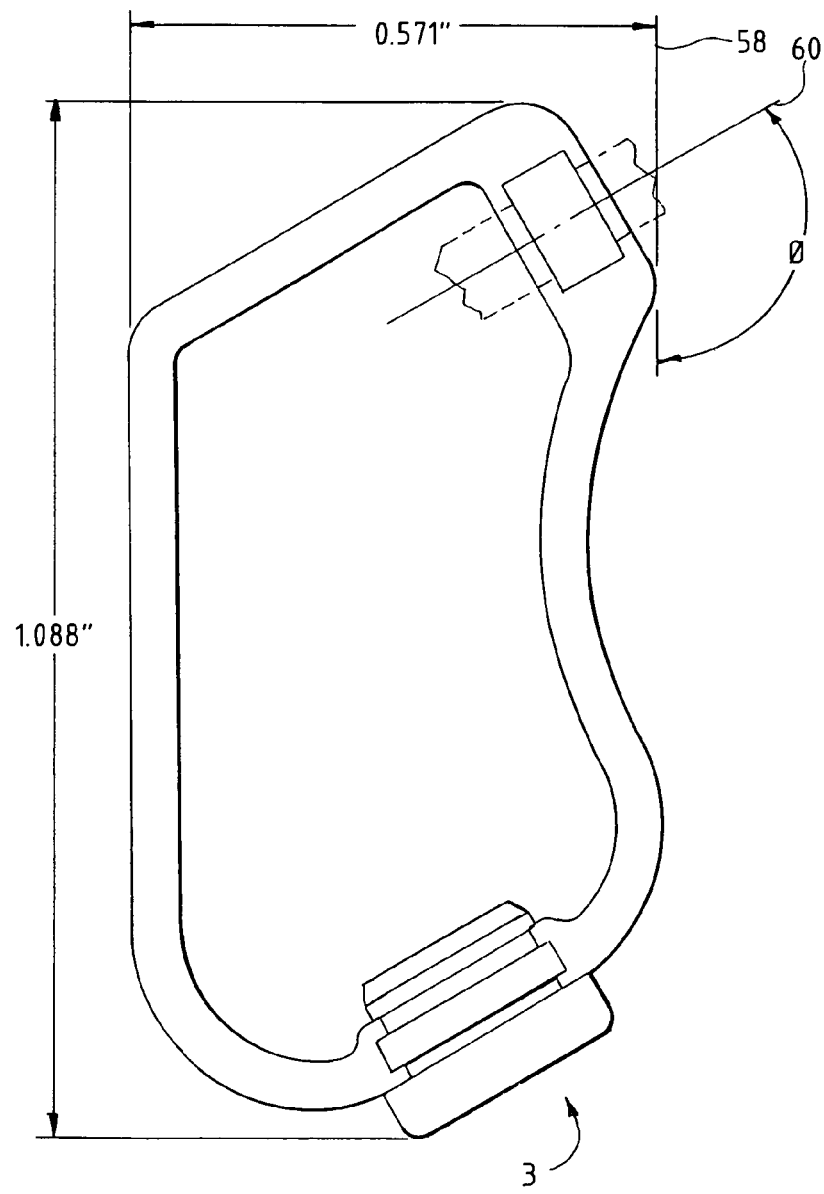
FIG. 2 illustrates a desirable configuration of one embodiment of the unitary housing built in accordance with the present invention.

FIG. 2 illustrates a desirable configuration of one embodiment of the unitary housing 3 built in accordance with the present invention. Angle theta from the vertical axis 58 to a longitudinal axis 60 of the tube nipple 9 is optimized for the typical ear canal, and allows the unitary housing 3 to hang vertically along the side of a user's head when worn. Angle theta is an obtuse angle and may be, for example, 118°.

FIG. 3 illustrates detail of one embodiment of the eartip 39 of FIG. 1. As is apparent from FIG. 3, and as mentioned above, flexible eartip 39 comprises a tube portion 41 and a foam portion 42. The tube portion 41 is flexible and may be PVC-105 tubing. The tube portion 41 extends through foam portion 42 such that sound passes through foam portion 42 via tube portion 41, and enters the inner ear when the foam portion 42 is fitted within the ear canal of a user. The foam portion 42 generally provides an acoustic seal with the ear canal and provides sufficient attenuation of background noise levels for audiometric testing.

As can be seen from FIG. 3, eartip 39 (and thus tube portion 41) may have a total length dimension of 26 mm, and the foam portion 42 may have a total length dimension of 13 mm. Because of the short length of the tube portion 41, even though it is flexible, a user may grasp the unitary housing 3 and use the unitary housing 3 as a convenient handle for inserting the foam portion 42 into the ear canal for sealing therewith.

FIG. 4 illustrates detail of one embodiment of the socket 13 of FIG. 1. The socket 13 may have the dimensions shown in FIG. 4.

Figure 5:
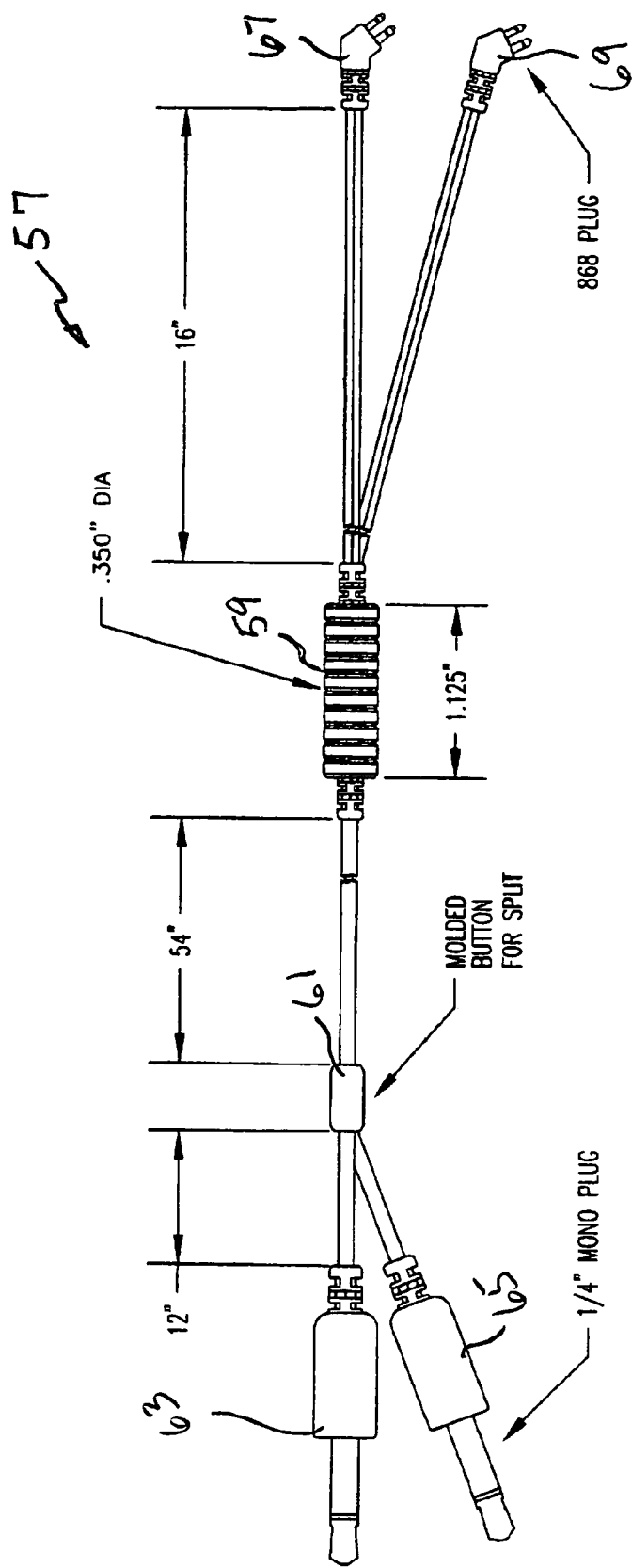
FIG. 5 illustrates one embodiment of the cable of FIG. 1.

FIG. 5 illustrates one embodiment of the cable 57 of FIG. 1. Cable 57 includes a pod 59, button 61, mono plugs 63 and 65, and plugs 67 and 69. Plugs 63 and 65 plug into an audio signal source, such as for example, an audiometer. Plugs 67 and 69 plug into respective earphone assemblies 1, one for each ear. Specifically, plug 67 mates with socket 13 of unitary housing 3 of one earphone assembly 1, and plug 69 mates with socket 13 of unitary housing 3 of another earphone assembly 1.

Figure 6:
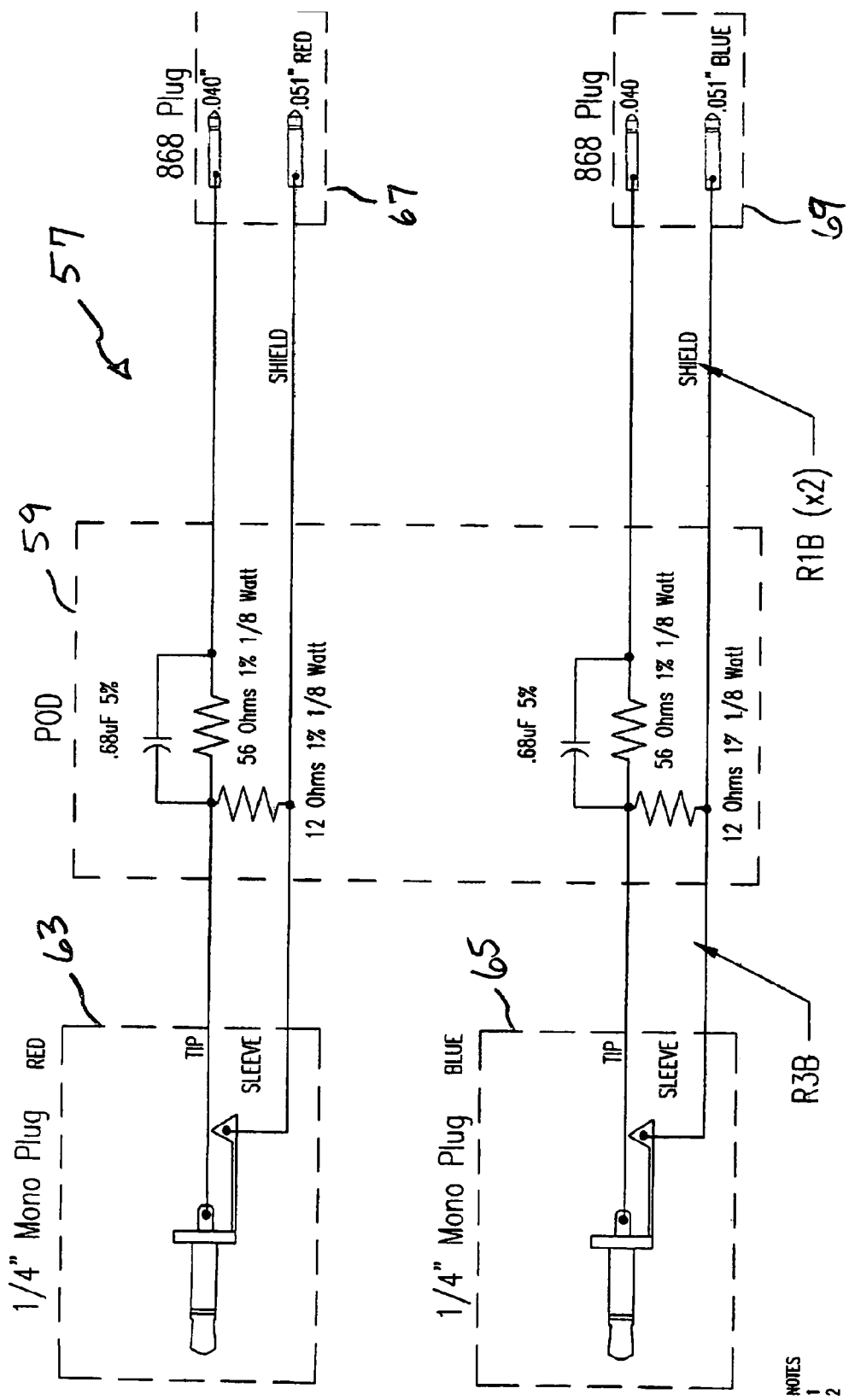
FIG. 6 illustrates electrical connections and equalization circuitry for the embodiment of the cable illustrated in FIG. 5.

FIG. 6 illustrates electrical connections and equalization circuitry for the embodiment of the cable 57 illustrated in 5. While the equalization circuitry is shown as being located in pod 59 of cable 57, it may also be located in unitary housing 3 of FIG. 1 or plugs 63 and 65 of cable 57.

FIG. 7 illustrates an alternate embodiment of the tube nipple of the eartip assembly of the present invention. Tube nipple 70 may have the dimensions as shown in FIG. 7.

Figure 8:
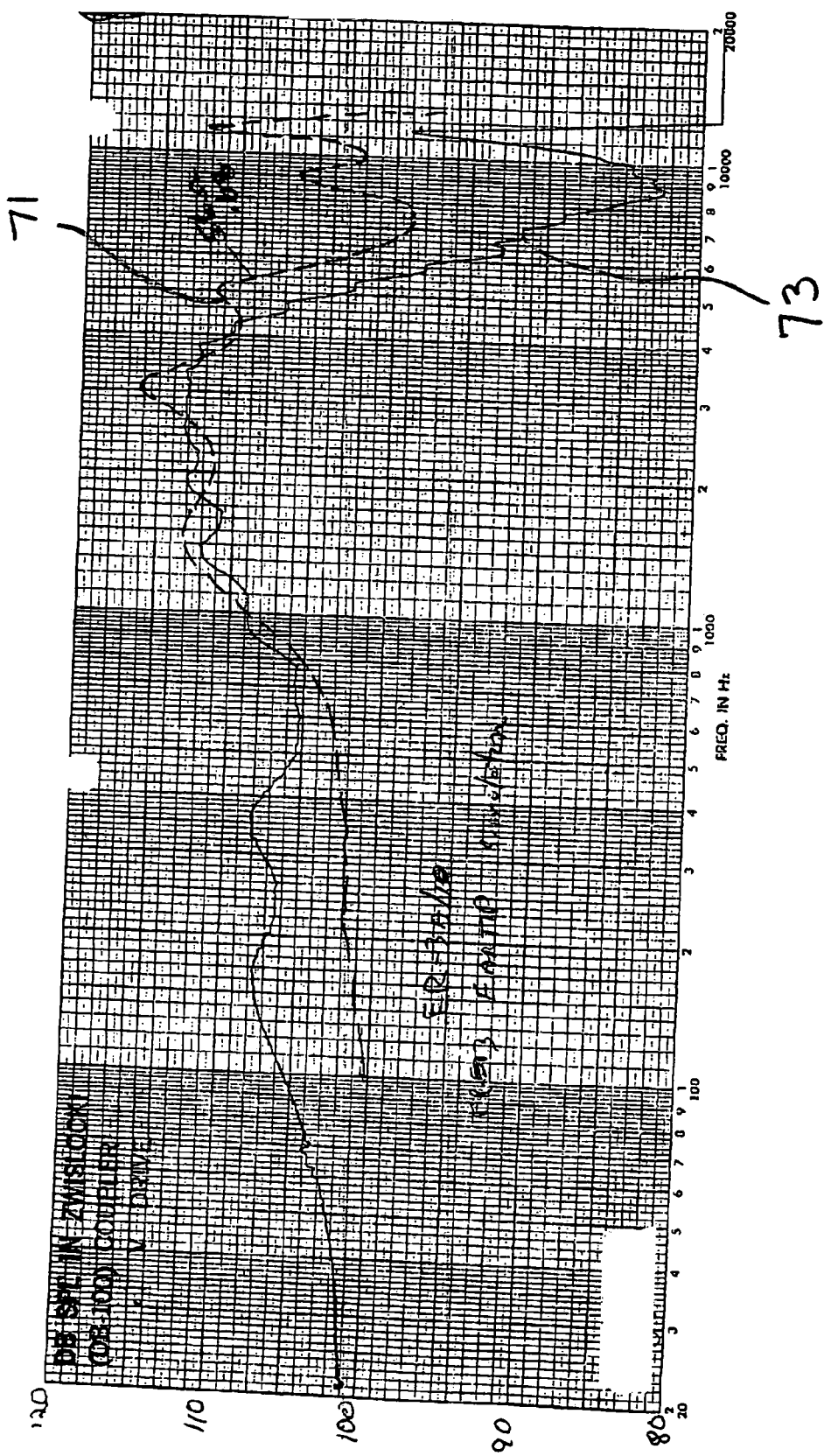
FIG. 8 illustrates the frequency response of the eartip assembly of the present invention, as compared to a prior art earphone device.

FIG. 8 illustrates the frequency response of the eartip assembly 1 of FIG. 1. Curve 71 shows the response of the eartip assembly 1 using the equalization circuitry of FIG. 6. For comparison, curve 73 shows the response of the prior art eartip mentioned above, i.e., the ER-3A of Etymotic Research Inc. As can be seen from FIG. 8, the present invention provides a better high frequency response than the ER-3A prior art eartip.

Figure 9:
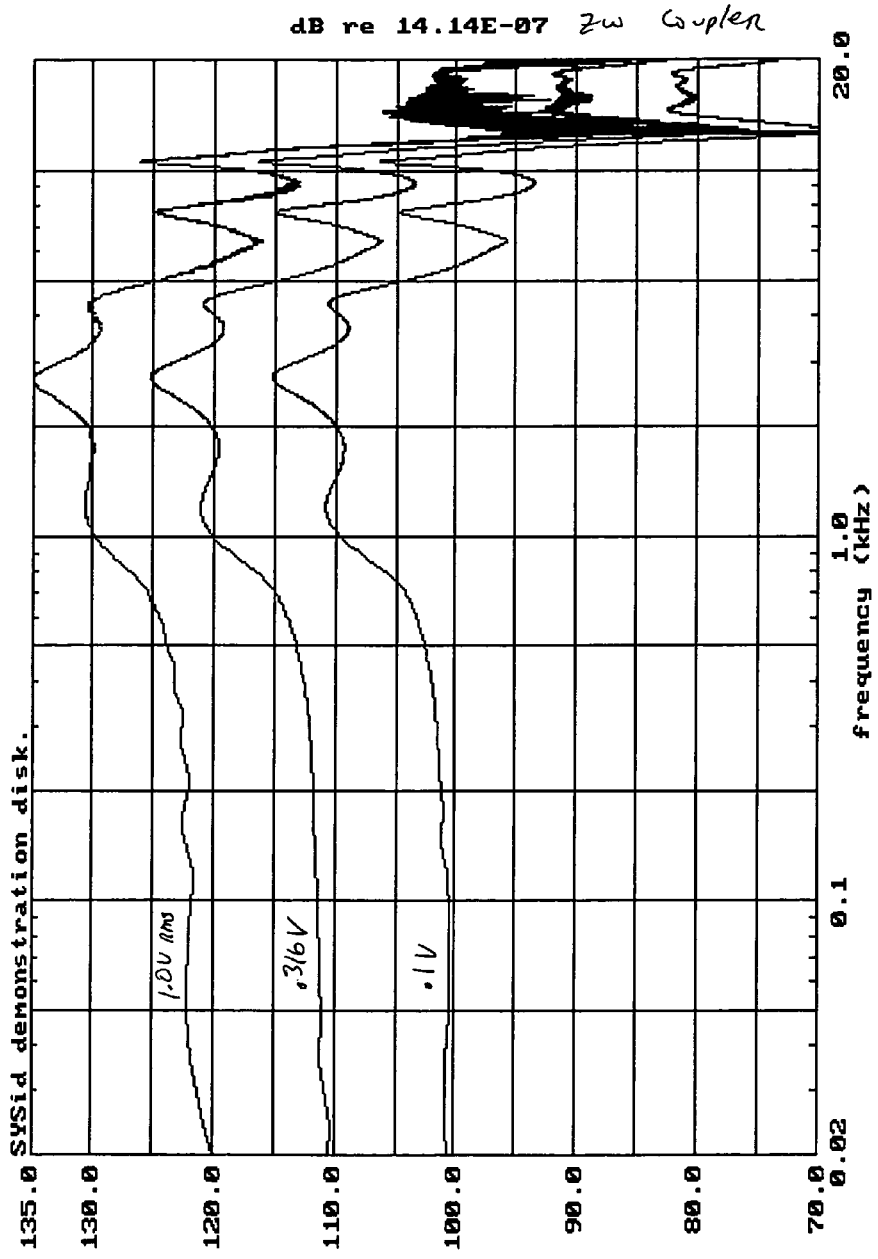
FIG. 9 illustrates frequency response curves of the insert earphone assembly of the present invention.

FIG. 9 illustrates frequency response curves of the insert earphone assembly of the present invention. The curves of FIG. 9 are similar to those mentioned above with respect to FIG. 1A for the prior art ER-3 earphone device. As can be seen from a comparison of FIG. 1A and FIG. 9, the present invention provides a better undistorted output at higher frequencies (i.e., at greater than approximately 6–8 kHz) and a better high frequency response than the prior art ER-3 device. In addition, the present invention maintains desired noise isolation and has a low occlusion effect relative to the prior art.

Figure 10:
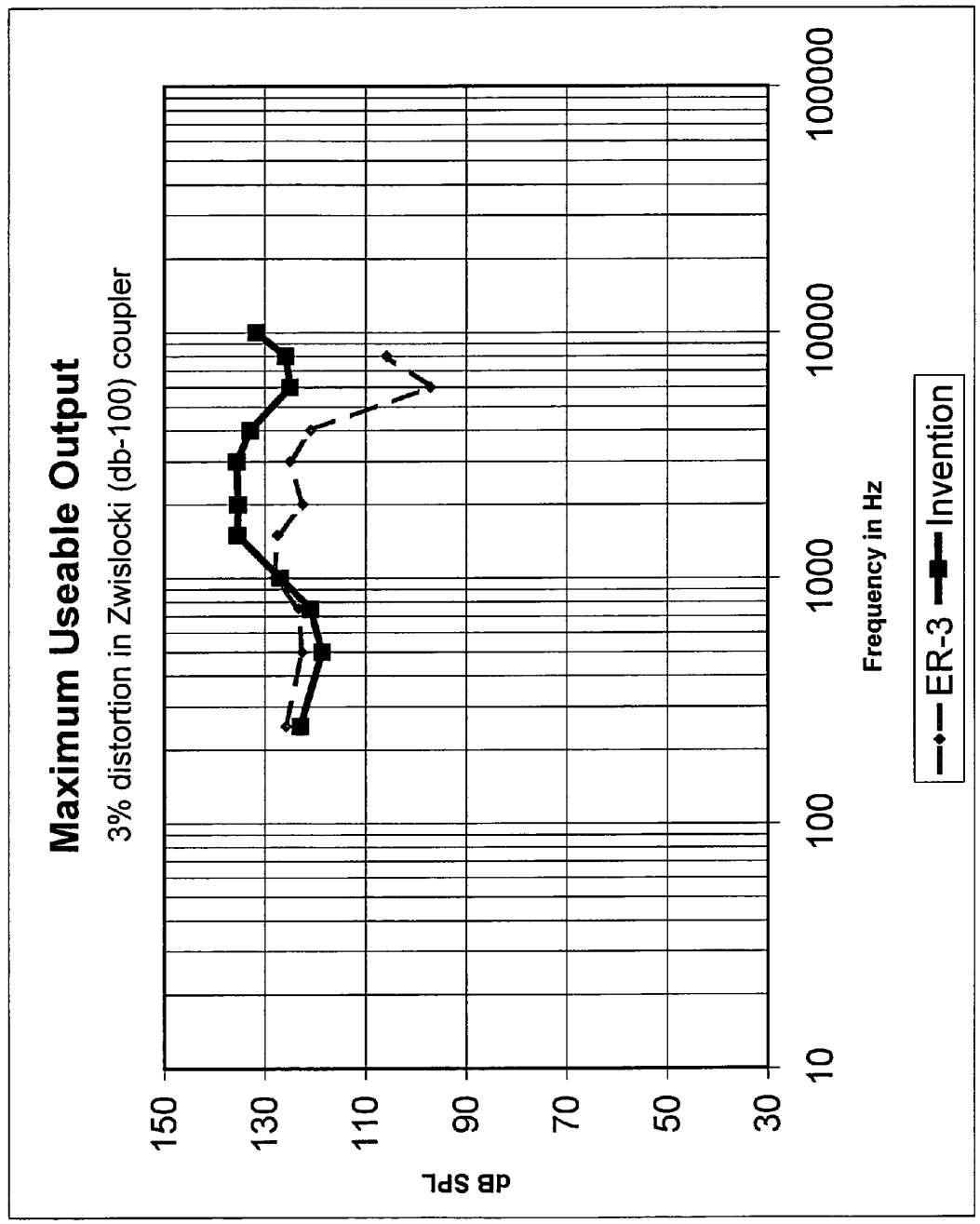
FIG. 10 illustrates the maximum undistorted output of the invention compared to that of a prior art device.

The present invention therefore solves the collapsed canal problem as achieved by the prior art ER-3, but provides a TDH-39 prior art like response shape at higher frequencies than the ER-3 within the calibration range of standard audiometers. Just as important, the maximum undistorted output (i.e., having ≦3% THD) at 6 and 8 kHz is approximately 20–25 dB greater with the present invention than is possible with the prior art ER-3, as shown in FIG. 10. In other words, the present invention has a response approximately 0 dB relative to TDH-39 and a sensitivity within range of the TDH-39 standard, unlike the ER-3. This is achieved by an assembly that is much more compact and is much cheaper and easier to manufacture than the prior art ER-3. In addition, because of its unique angle (as discussed above with respect to FIG. 2) and its compact design, the assembly of the present invention is more comfortable to wear than both the prior art TDH-39 and ER-3.

In view of the above-detailed description of the present invention and associated drawings, other modifications and variations will now become apparent to those skilled in the art. It should also be apparent that such modifications and variations may be effected without departing from the spirit and scope of the present invention.

What is claimed and desired to be secured by Letters Patent is:

1. An insert earphone comprising:
    a housing;
    a receiver located in the housing and having an output port, the receiver for electrically coupling with an audio signal source;
    a flexible eartip for acoustic sealing with an ear canal of a user; and
    a tube nipple providing an acoustic pathway through at least one wall of the housing and having a first end and a second end, the first end being located within the housing and being acoustically coupled to the output port of the receiver and the second end being located externally to the housing and being acoustically coupled to the flexible eartip, the tube nipple and housing being configured and arranged to form an obtuse angle between a longitudinal axis of the tube nipple and a vertical axis of the housing where the tube nipple meets the housing, wherein the housing hangs approximately vertically along the side of a user's head when worn; and
    wherein the insert earphone is inserted at least partially into the ear canal and is supported entirely by the ear canal when worn by the user.

2. The insert earphone of claim 1 wherein the angle is approximately 118 degrees.

3. The insert earphone of claim 1 further comprising a flexible channel located between the output port of the receiver and the first end of the tube nipple.

4. The insert earphone of claim 3 wherein the flexible channel has a first end and a second end, and wherein the first end of the flexible channel is coupled to output port of the receiver and the second end of the flexible channel is coupled to the first end of the tube nipple.

5. The insert earphone of claim 1 wherein the flexible eartip comprises a flexible tube portion and a foam eartip portion, and wherein at least a portion of the flexible tube portion extends through the foam eartip portion.

6. The insert earphone of claim 5 wherein the tube nipple is rigid and wherein the second end of the tube nipple is positioned within the flexible tube portion of the flexible eartip.

7. The insert earphone of claim 1 further comprising an acoustic damper located in the tube nipple proximate the first end of the tube nipple.

8. An insert earphone comprising:
    a housing;
    a receiver located in the housing and having an output port, the receiver for electrically coupling with an audio signal source;

a flexible eartip for acoustic sealing with an ear canal of a user, the flexible eartip having a foam eartip portion and a flexible tube portion;

a rigid tube nipple providing an acoustic pathway through at least one wall of the housing and having a first end and a second end, the first end of the rigid tube nipple being located within the housing and being acoustically coupled to the output port of the receiver and the second end of the rigid tube nipple being located externally to the housing and being acoustically coupled to flexible tube portion of the flexible eartip; and a flexible channel located between the output port of the receiver and the first end of the rigid tube nipple; and wherein the insert earphone is inserted at least partially into the ear canal and is supported entirely by the ear canal when worn by the user.

9. The insert earphone of claim 8 wherein the flexible channel has a first end and a second end, and wherein the first end of the flexible channel is coupled to the output port of the receiver and the second end of the flexible channel is coupled to the first end of the rigid tube nipple.

10. An insert earphone comprising:

a housing;

a receiver located in the housing and having an output port, the receiver for electrically coupling with an audio signal source;

a flexible eartip for acoustic sealing with an ear canal of a user; and a tube nipple providing an acoustic pathway through at least one wall of the housing and having a first end and a second end, the first end being located within the housing and being acoustically coupled to the output port of the receiver and the second end being located externally to the housing and being acoustically coupled to the flexible eartip, the tube nipple and housing being configured and arranged to form an obtuse angle of approximately 118 degrees between a longitudinal axis of the tube nipple and a vertical axis of the housing, wherein the housing hangs approximately vertically along the side of a user's head when worn.

11. The insert earphone of claim 10 further comprising a flexible channel located between the output port of the receiver and the first end of the tube nipple.

12. The insert earphone of claim 11 wherein the flexible channel has a first end and a second end, and wherein the first end of the flexible channel is coupled to output port of the receiver and the second end of the flexible channel is coupled to the first end of the tube nipple.

13. The insert earphone of claim 10 wherein the flexible eartip comprises a flexible tube portion and a foam eartip portion, and wherein at least a portion of the flexible tube portion extends through the foam eartip portion.

14. The insert earphone of claim 13 wherein the tube nipple is rigid and wherein the second end of the tube nipple is positioned within the flexible tube portion of the flexible eartip.

15. The insert earphone of claim 10 further comprising an acoustic damper located in the tube nipple proximate the first end of the tube nipple.

16. An insert earphone comprising:

a housing;

a receiver located in the housing and having an output port, the receiver for electrically coupling with an audio signal source;

a flexible eartip for acoustic sealing with ear canal of a user;

a tube nipple having a first end and a second end, the first end located within the housing and acoustically coupled to the output port of the receiver and the second end located externally to the housing and acoustically coupled to the flexible eartip, the tube nipple and the housing being configured and arranged to form an obtuse angle of approximately 118 degrees between a longitudinal axis of the tube nipple and a vertical axis of the housing, wherein the housing hangs approximately vertically along the side of a user's head when worn; and an acoustic damper located in the tube nipple proximate the first end of the tube nipple.

17. The insert earphone of claim 16 wherein the flexible eartip comprises a flexible tube portion and a foam eartip portion, and wherein at least a portion of the flexible tube portion extends through the foam eartip portion.

18. The insert earphone of claim 17 wherein the tube nipple is rigid and wherein the second end of the tube nipple is positioned within the flexible tube portion of the flexible eartip.

19. The insert earphone of claim 16 further comprising a flexible channel located between the output port of the receiver and the first end of the tube nipple.

20. The insert earphone of claim 19 wherein the flexible channel has a first end and a second end, and wherein the first end of the flexible channel is coupled to the output port of the receiver and the second end of the flexible channel is coupled to the first end of the tube nipple.

21. An insert earphone comprising:

a housing;

a receiver located in the housing and having an output port, the receiver for electrically coupling with an audio signal source;

a flexible eartip for acoustic sealing with an ear canal of a user, the flexible eartip having a foam eartip portion and a flexible tube portion; and a tube nipple providing an acoustic pathway through at least one wall of the housing and having a first end and a second end, the first end of the tube nipple being located within the housing and being acoustically coupled to the output port of the receiver and the second end of the tube nipple being located externally to the housing and being acoustically coupled to the flexible tube portion of the flexible eartip;

the tube nipple and the housing being configured and arranged to form an obtuse angle between a longitudinal axis of the tube nipple and a vertical axis of the housing, wherein the housing hangs approximately vertically along the side of a user's head when worn;

wherein the earphone providing a response that is approximately 0 dB relative to a response of the TDH-39 standard at at least one of 6 and 8 khz, and wherein the second end of the tube nipple is positioned within the flexible tube portion of the flexible eartip.

22. The insert earphone of claim 21, wherein the angle is approximately 118 degrees.

23. The insert earphone of claim 21, further comprising a flexible channel located between the output port of the receiver and the first end of the tube nipple.

24. The insert earphone of claim 23, wherein the flexible channel has a first end and a second end, and wherein the first end of the flexible channel is coupled to the output port of the receiver and the second end of the flexible channel is coupled to the first end of the tube nipple.

25. The insert earphone of claim 21, further comprising an acoustic damper located in the tube nipple proximate the first end of the tube nipple.

26. An insert earphone comprising:
a housing;
a receiver located in the housing and having an output port, the receiver for electrically coupling with an audio signal source;
a flexible eartip for acoustic sealing with ear canal of a user;
a tube nipple having a first end and a second end, the first end located within the housing and acoustically coupled to the output port of the receiver and the second end located externally to the housing and acoustically coupled to the flexible eartip;
an acoustic damper located in the tube nipple proximate the first end of the tube nipple,
wherein the insert earphone is inserted at least partially into the ear canal and is supported entirely by the ear canal when worn by the user, and wherein the tube nipple and the housing being configured and arranged to form an obtuse angle between a longitudinal axis of the tube nipple and a vertical axis of the housing where the tube nipple meets the housing.

27. The insert earphone of claim 26, wherein the angle is approximately 118 degrees.

28. The insert earphone of claim 26, wherein the flexible eartip comprises a flexible tube portion and a foam eartip portion, and wherein at least a portion of the flexible tube portion extends through the foam eartip portion.

29. The insert earphone of claim 28, wherein the tube nipple is rigid and wherein the second end of the tube nipple is positioned within the flexible tube portion of the flexible eartip.

30. The insert earphone of claim 26, further comprising a flexible channel located between the output port of the receiver and the first end of the tube nipple.

31. The insert earphone of claim 30, wherein the flexible channel has a first end and a second end, and wherein the first end of the flexible channel is coupled to the output port of the receiver and the second end of the flexible channel is coupled to the first end of the tube nipple.

* * * * *